(12) United States Patent
Harschack et al.

(10) Patent No.: US 11,324,553 B2
(45) Date of Patent: May 10, 2022

(54) SIDE FIRE OPTICAL FIBER FOR HIGH POWER APPLICATIONS

(75) Inventors: Alexander Harschack, Bad Honnef (DE); Wolfgang Neuberger, F.T. Labuan (MY); Kelly Moran, Wilbraham, MA (US)

(73) Assignee: Biolitec Unternehmensbeteilgungs II AG, Vienna (AT)

( * ) Notice: Subject to any disclaimer, the term of this patent is extended or adjusted under 35 U.S.C. 154(b) by 2585 days.

(21) Appl. No.: 11/592,598

(22) Filed: Nov. 3, 2006

(65) Prior Publication Data

US 2007/0106286 A1 May 10, 2007

Related U.S. Application Data

(60) Provisional application No. 60/736,107, filed on Nov. 10, 2005.

(51) Int. Cl.
*A61B 18/22* (2006.01)
*G02B 6/028* (2006.01)
*A61B 18/20* (2006.01)

(52) U.S. Cl.
CPC .......... *A61B 18/22* (2013.01); *A61B 18/20* (2013.01); *G02B 6/0283* (2013.01); *A61B 2018/2244* (2013.01)

(58) Field of Classification Search
CPC .......... A61B 18/22; A61B 2018/2277; G02B 6/262; G02B 6/0283; G02B 6/03627
USPC .... 606/15, 13, 16; 385/84, 144, 123, 76–79; 372/6; 65/395, 397
See application file for complete search history.

(56) References Cited

U.S. PATENT DOCUMENTS 4,698,084 A * 10/1987 Severijns et al. .............. 65/412
4,740,047 A 4/1988 Abe et al.
(Continued)

FOREIGN PATENT DOCUMENTS

JP 3-63377 9/1991

OTHER PUBLICATIONS

Kawakami S., Nishida S., Characteristics of a doubly clad optical fiber with a low-index inner cladding, Quantum Electronics, IEEE Journal of, Dec. 1974, vol. 10, Issue 12, p. 880.*
(Continued)

*Primary Examiner* — Boniface N Nganga
(74) *Attorney, Agent, or Firm* — BJ Associates; Bolesh J. Skutnik

(57) ABSTRACT

A side fire optical fiber tip is provided for use in high power laser applications having outputs of greater than or equal to 50 Watts. A predetermined length of an output tip on the distal end of the optical fiber is formed with an optical fiber core and cladding layer of preselected thickness wherein the cladding to core diameter ratio is at least as great as 1.2. A side fire surface is formed on the distal end of the core/clad output end. Over this optical fiber output end, a pure silica capillary tube is fused to the predetermined length of exposed cladding where the outermost cladding is also pure silica to reduce thermal mismatch during the fusion process. By having the refractive index at the fusing interface matched, and bubbles or gaps eliminated or prevented, it is possible to substantially eliminate Fresnel reflection losses at this interface.

11 Claims, 3 Drawing Sheets

(56) References Cited

U.S. PATENT DOCUMENTS

| | | | | |
|---|---|---|---|---|
| 5,033,304 | A | * | 7/1991 | Rosen .................... G01N 29/07 73/597 |
| 5,164,945 | A | * | 11/1992 | Long ...................... A61B 18/22 372/6 |
| 5,257,989 | A | * | 11/1993 | Celaya ................... A61B 18/24 606/15 |
| 5,292,320 | A | | 3/1994 | Brown et al. |
| 5,349,590 | A | * | 9/1994 | Amirkhanian ......... A61B 18/22 372/6 |
| 5,428,699 | A | | 6/1995 | Pon |
| 5,437,660 | A | | 8/1995 | Johnson et al. |
| 5,470,330 | A | * | 11/1995 | Goldenberg et al. ............. 606/7 |
| 5,509,917 | A | | 4/1996 | Cecchetti et al. |
| 5,562,657 | A | * | 10/1996 | Griffin ................ A61B 18/245 606/13 |
| 5,638,483 | A | * | 6/1997 | Konwitz ......................... 385/38 |
| 5,772,657 | A | * | 6/1998 | Hmelar et al. ................... 606/15 |
| 5,991,486 | A | * | 11/1999 | Braglia ......................... 385/123 |
| 6,222,970 | B1 | * | 4/2001 | Wach et al. .................... 385/115 |
| 6,535,671 | B1 | * | 3/2003 | Poole ................... G02B 6/2852 385/32 |
| 6,554,824 | B2 | | 4/2003 | Davenport et al. |
| 6,802,838 | B2 | | 10/2004 | Loeb et al. |
| 7,447,409 | B2 | | 11/2008 | Griffin |
| 2002/0031320 | A1 | * | 3/2002 | Nagayama ........ C03B 37/01413 385/127 |
| 2002/0094159 | A1 | * | 7/2002 | Goldberg et al. ................ 385/27 |
| 2002/0097970 | A1 | * | 7/2002 | Sasaoka ........................ 385/123 |
| 2003/0024276 | A1 | * | 2/2003 | Anderson et al. .............. 65/390 |
| 2003/0103747 | A1 | * | 6/2003 | Cho et al. ..................... 385/124 |
| 2004/0114892 | A1 | * | 6/2004 | Chiang et al. ................. 385/123 |
| 2004/0156401 | A1 | * | 8/2004 | Sandrock et al. ................ 372/6 |
| 2005/0232571 | A1 | * | 10/2005 | Fabian .......................... 385/144 |
| 2006/0239625 | A1 | * | 10/2006 | Ishikawa et al. .............. 385/115 |

OTHER PUBLICATIONS

Kuo et al., "Holmium Laser Enucleation of the Prostate (HoLEP): A Technical Update" Jun. 6, 2003, World Journal of Surgical Oncology, I :6 (pp. 1-9).*

* cited by examiner

300

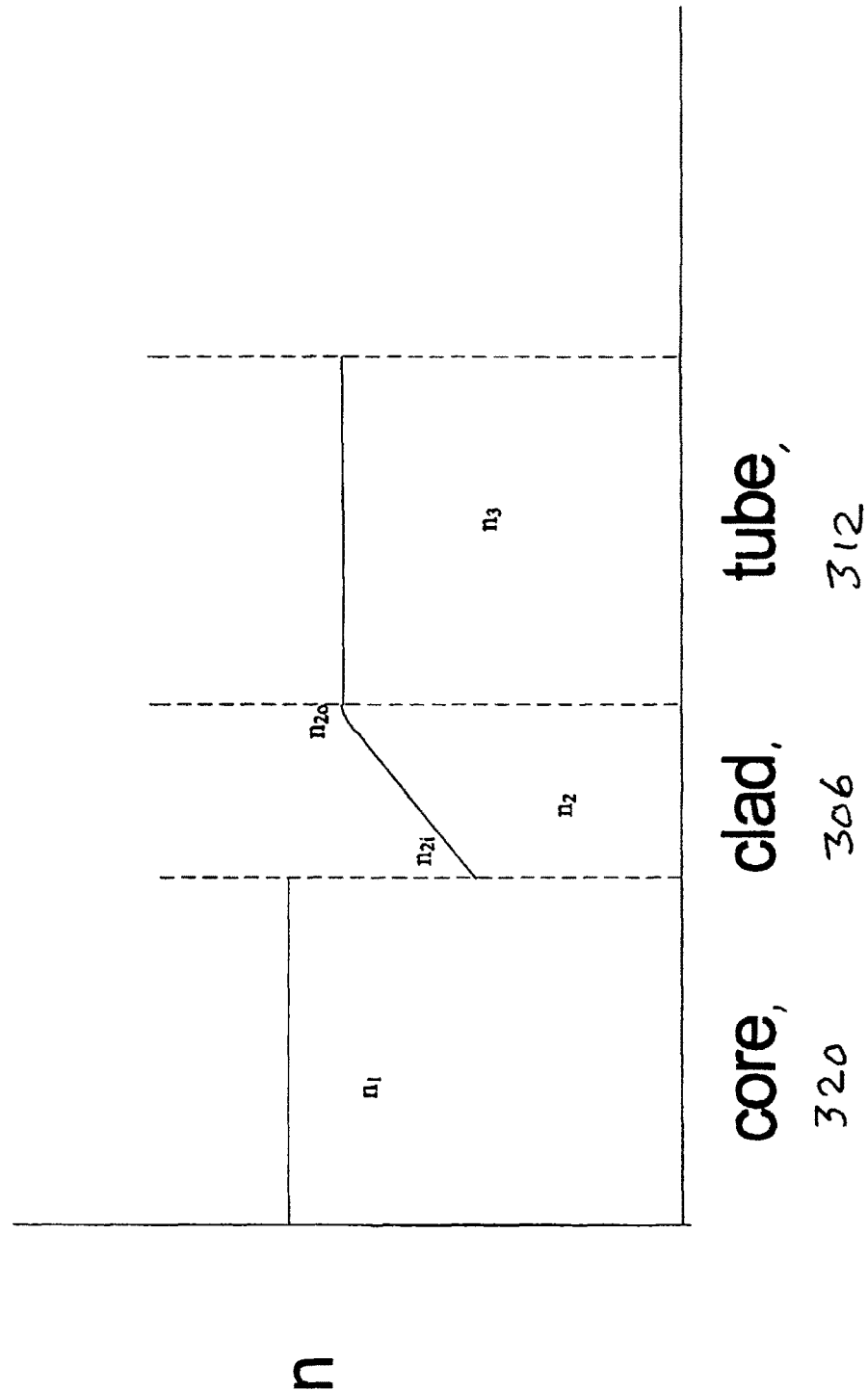

SIDE FIRE OPTICAL FIBER FOR HIGH POWER APPLICATIONS

DOMESTIC PRIORITY UNDER 35 USC 119(E)

This application claims the benefit of U.S. Provisional Application Ser. No. 60/736,107, filed Nov. 10, 2005, which is incorporated by reference herein.

BACKGROUND OF THE INVENTION

Field of the Invention

The present invention relates generally to the field of the medical treatment using laser energy, and, further, relates to the transmission of high power laser energy over an optical fiber through an side-firing output end modified according to the present invention, and, more specifically, relates to the medical treatment of benign prostate hyperplasia with a side fire optical fiber tip.

Invention Disclosure Statement

Benign prostatic hyperplasia (BPH) or "enlarged prostate" refers to the non-cancerous (benign) growth of the prostate gland. While BPH is the most common prostate problem in men over 50 years of age, benign growth of the prostate begins with microscopic nodules around 25 years of age but rarely produces symptoms before a man reaches age 40. It is estimated that 6.3 million men in the United States alone have BPH and the disease is responsible for 6.4 million doctor visits and more than 400,000 hospitalizations per year.

The exact cause of BPH is unknown but it is generally thought to involve hormonal changes associated with the aging process. Testosterone likely has a role in BPH as it is continually produced throughout a man's lifetime and is a precursor to dihydrotestosterone (DHT) which induces rapid growth of the prostate gland during puberty and early adulthood. When fully developed, the prostate gland is approximately the size of a walnut and remains at this size until a man reaches his mid-forties. At this point the prostate begins a second period of growth which for many men often leads to BPH later in life.

In contrast to the overall enlargement of the gland during early adulthood, benign prostate growth occurs only in the central area of the gland called the transition zone, which wraps around the urethra. As this area of the prostate grows, the gland presses against the urethra and causes a number of lower urinary tract symptoms (LUTS) such as difficult urination (obstructive symptoms) and painful urination (storage symptoms). Eventually, the bladder itself weakens and loses the ability to empty itself.

Obstructive symptoms such as intermittent flow or hesitancy before urinating can severely reduce the volume of urine being eliminated from the body. If left untreated, acute urine retention can lead to other serious complications such as bladder stones, urinary tract infections, incontinence, and, in rare cases, bladder damage, kidney damage. These complications are more prevalent in older men who are also taking anti-arrhythmic drugs or anti-hypertensive (non-diuretic) medications. In addition to the physical problems associated with BPH, many men also experience anxiety and a reduced quality of life.

Mild symptoms of BPH are most often treated with medication such as alpha-blockers and anti-androgens. Men suffering with moderate to severe BPH symptoms typically must undergo surgery. Transurethral resection of the prostate (TURP) is the standard surgical procedure, although there are a number of other surgical approaches available as well. Other less invasive surgical methods include: transurethral incision of the prostate (TUIP), transurethral microwave thermotherapy (TUMT), transurethral electro vaporization (TUVP), transurethral needle ablation (TUNA), and laser surgery.

There are a number of different laser techniques in which light is used to eliminate excess prostate tissue either by ablation (vaporization) or thermal coagulation mechanisms. The observed clinical effects are due to the absorption of light (by the target tissue itself and/or surrounding fluids) and subsequent heat transfer, the extent of which largely depends on the power and wavelength of the laser beam. In general, wavelength determines the depth of tissue penetration while power has a direct influence on the temperature created within the tissue. However, it is temperature that determines the ultimate impact at the treatment area since tissue must be heated to greater than 50 C to induce coagulation whereas vaporization occurs at temperatures over 100 C. Temperature also impacts morbidity, namely inflammation, dysuria, bleeding, and the need and duration of post-treatment catheterization.

Laser approaches currently in use for the treatment of BPH utilize a single wavelength of light to eliminate excess prostate tissue via ablation or by inducing coagulation necrosis. Initially, however, laser surgeries for BPH used the Holmium:YAG laser in combination with the Nd:YAG laser in a treatment method called Combination Endoscopic Laser Prostatectomy (CELAP) being a two step process where the Holmium laser was used to create the channel through the prostate and the Nd laser was used for coagulation. It was further determined that the Nd laser was unnecessary if the Holmium laser was defocused for coagulation purposes. For the CELAP procedure, the Holmium laser was used to create a channel in the prostate by vaporizing the tissue after which, the Nd:YAG laser was used to further eliminate tissue via coagulation. CELAP has been replaced by newer, single-wavelength laser methods which are still being evaluated for long-term efficacy.

Holmium Laser Enucleation of the Prostate or HoLEP is a laser ablation technique in which a 2140 nm Ho:YAG laser is used to remove whole lobes from the prostate. Specifically, HoLEP uses a bare optical fiber which is brought into direct contact with the target tissue. Enucleation occurs when the vapor bubbles that form in front of the fiber bombard the target tissue and tear it apart. Special morcellators or other extraction techniques are needed to remove tissue debris from the area. The efficacy of the HoLEP procedure depends upon maintaining very close contact between the fiber and the tissue to be removed. As a result, it is possible to perforate the prostate during the procedure and many surgeons avoid using HoLEP because of the difficulty in learning and maintaining proficiency in the technique.

Another laser technique to eliminate prostate overgrowth features a frequency-doubled Nd:YAG laser as a pulsed, 532 nm high-power potassium-titanyl-phosphate laser (KTP) that vaporizes target tissue as well as induces thin layers of coagulation in the surrounding tissues as described by Davenport et al. in U.S. Pat. No. 6,554,824. The 532 nm radiation used in KTP is selectively absorbed by hemoglobin and penetrates tissues only to a depth of 1-2 mm. Moreover, this method requires continuous irrigation of the treatment site to cool the tissue during the procedure to help reduce unwanted coagulation necrosis in deeper tissue layers.

Much like TURP, most types of laser surgeries are able to provide an immediate improvement in the urinary stream. Laser surgery for BPH has other potential advantages such as reduced blood loss as well as shorter treatment times, faster patient recovery, and a lower risk of post-treatment incontinence. However, many patients still require catheterization for 1-2 weeks post-treatment after undergoing some forms of laser surgery. Despite the obvious benefits of laser procedures for BPH, long-term follow-up studies on the clinical results of many laser techniques are not yet widely available.

To date, none of the less invasive procedures have proven to be more effective than TURP nor are they generally appropriate across all patient groups including: younger men, debilitated elderly patients, patients with severe medical conditions including uncontrolled diabetes, cirrhosis, active alcoholism, obesity, and heart disease, as well as men taking blood thinning medications. As such, there remains a need for a device and treatment method for the effective alleviation of BPH symptoms that can be used across all patient groups with a minimum of adverse complications post-treatment. The present invention is directed towards this need.

U.S. Pat. No. 4,740,047 to Hitachi Cable et al. discusses the disadvantages of a side fire fiber where the fiber is placed in a transparent tubular member. As noted the several disadvantages are an air layer between the fiber and the tubular member resulting in leaking beams, multiple reflections, breakage of the tip, and in the use of this fiber tip in a front-view type of endoscope. The irradiation probe shown has a lateral beaming fiber with conventional cladding with an air space about the tip. The tubular member is attached to the fiber by means of several coatings of plastic material for the purpose of reducing direct external forces on the fiber. In order to prevent leaking beams, anti-reflective coatings are applied to the external surface of the tubular member in flat areas on the tubular member. The present invention reduces or eliminates these problems.

U.S. Pat. No. 5,292,320 to Brown et al. discloses another side firing output end having multiple side fire surfaces within the fiber core and is incorporated by reference. The fiber core has a plurality of grooves as well as a slanted end surface for reflecting laser energy in a lateral manner. The core is glued into the end cap. Under high power laser operations, for example, 50 W or greater, this output end fails.

U.S. Pat. No. 5,437,660 to Johnson et al. discloses a device for treating the body with a side fire feature thereon and is incorporated by reference. An end cap having a reflective surface therein is attached over the end of the fiber.

U.S. Pat. No. 5,509,917 to Cecchetti et al. discloses a lateral beaming laser tip having a transparent quartz cap about the output end of the optical fiber therein and is incorporated by reference. In contrast to the present invention, the tip has an extended section of optical core placed into the cap with an air gap about the core. Further, the cap is shown having various focusing means for the laser radiation reflected off of the slanted end surface of the optical core. This laser tip is very complex to manufacture and to achieve the very same structures each time.

U.S. Pat. No. 6,554,824 to Davenport et al. discloses a treatment means for a prostrate gland also having a side fire feature as noted in figures and is incorporated by reference. The actual construction of the tip is not disclosed.

U.S. Pat. No. 6,802,838 to Loeb et al. discloses another side fire laser fiber enclosed within a tube with circulating fluid thereabout and is incorporated by reference. As noted the tube being the cap is placed over the bared distal end portion of the optical fiber by thermal fusion or to a buffer coat and vinyl cladding thereof by an adhesive.

There is thus a need for a laser treatment system that improves on the state of the art by allowing increased high power laser beam density transmission, high reliability of the output tip, and thereby providing increased power density available for medical treatments.

OBJECTIVES AND SUMMARY OF THE INVENTION

It is an objective of the present invention to provide a system that increases the beneficial aspects of the treatment of BPH, in particular, with high power laser energy by increasing the damage threshold of the optical fiber tip and by increasing the reliability of the laser tip.

It is another objective of the present invention to provide for the efficient treatment of certain medical conditions with the use of high power laser energy to a treatment or work site while maintaining laser beam quality.

It is yet another objective of the present invention to provide a side fire optical fiber tip being able to handle a high power laser with the tip having excellent durability.

It is still a further objective of the present invention to provide a side fire optical fiber tip for use with high power lasers, from about 50 to about 300 Watt applications, having a durable tip and further presenting a minimum of manufacturing problems.

Briefly stated, the present invention provides an optical fiber treatment system for high power laser transmission to an area of medical treatment. A side fire optical fiber tip for use in high power laser applications having outputs of greater than or equal to 50 Watts is a key to the system. Embodiments are particularly appropriate for the medical treatment of benign prostate hyperplasia (BPH) with a side fire optical fiber tip using a Holmium:YAG laser or a high power diode laser. Such procedures can be done with only local anesthesia. A predetermined length of an output tip on the distal end of the optical fiber of the present invention is formed with an optical fiber core and cladding layer of preselected thickness wherein the cladding to core diameter ratio is at least as great as 1.2. A side fire surface is formed on the distal end of the core/clad output end. Over this optical fiber output end, a pure silica capillary tube is fused to the predetermined length of exposed cladding where the outermost cladding is also pure silica to reduce thermal mismatch during the fusion process. By having the refractive index at the fusing interface of the tube to the cladding matched, and bubbles or gaps eliminated or prevented, it is possible to substantially eliminate Fresnel reflection losses at this interface. Further, the outer surface area where the laser energy is exiting from the tube may be heat treated with a laser to increase durability for high power laser energy transmission in fluid environments. Germanium-doped silica as well as pure silica can be used as fiber core material.

The above, and other objects, features and advantages of the present invention will become apparent from the following description read in conjunction with the accompanying drawings, (in which like reference numbers in different drawings designate the same elements).

BRIEF DESCRIPTION OF DRAWINGS

FIG. 4 illustrates, by way of example, the index of refractions of the core, clad and tube sections of the present invention.

DETAILED DESCRIPTION OF PREFERRED EMBODIMENTS

The present invention describes an optical fiber having a side fire tip that is useful for high power laser beam transmission through an optical fiber. The side fire tip is used in medical treatment and has high reliability.

The present invention provides a side fire optical tip for high power lasers, in particular, having outputs of greater than or equal to 50 Watts to about 300 Watts. The present invention is particularly appropriate for the medical treatment of benign prostate hyperplasia (BPH) with a side fire optical fiber tip with a Holmium:YAG laser.

Figure 1:
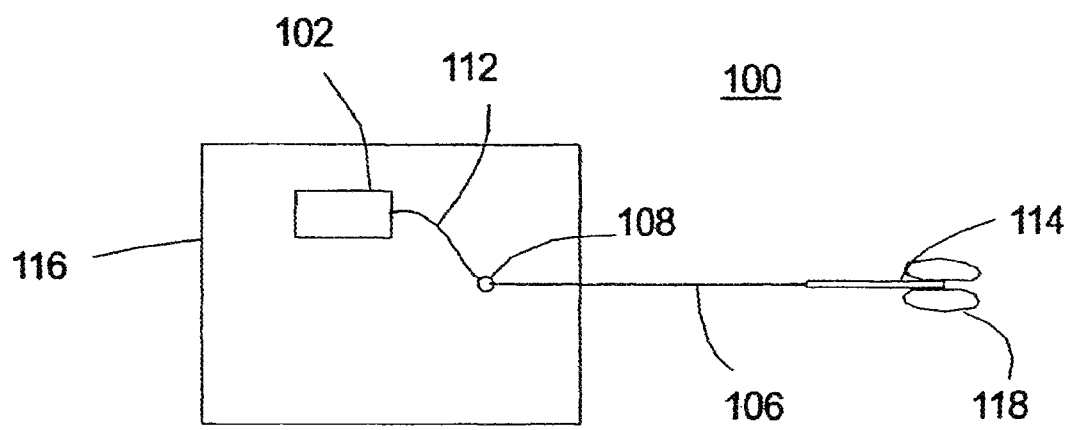
FIG. 1 illustrates by block diagram of a medical laser device using the present invention in the treatment of BPH.

FIG. 1 is a block diagram depicting one embodiment of medical laser device 100 in accord with the present invention. Device 100 includes one laser source. The preferred laser for the present invention is a Holmium:YAG laser, but other laser sources may be included such as a 980 nm laser. Laser source 102 outputs radiation into optical fiber 112. Connector 108 takes the input from optical fiber 112 and outputs the laser energy into output optical fiber 106 that delivers the radiation into output end 114. Device 100 further includes control device 116 where the operational parameters are input. These operational parameters would also include power, duration, repetition rate, and continuous or pulse mode, energy density, etc., for the laser therein. Output end 114 is shown within prostrate gland 118. A suitable catheter or endoscope device is used to place output end 114 with attached optical fiber 106 in the urethra up to the area of the surrounding prostate tissue of concern. Further other devices may be included in the catheter such as viewing means, irrigating means, cooling means, etc.

In a typical mode of operation, output end 114 irradiates the target area with a preselected pattern of pulses and energy densities. Treatment can also involve a semi-continuous irradiation for each position to be treated, or with a turning of the side firing fiber probe to circumferentially treat a larger section. In preferred embodiments, these patterns of pulses and energy result in the ablation of prostatic tissue as well as coagulation of underlying tissues to substantially eliminate blood loss beyond the removed tissue and with minimal thermal damage to deeper and surrounding tissue.

Figure 2:
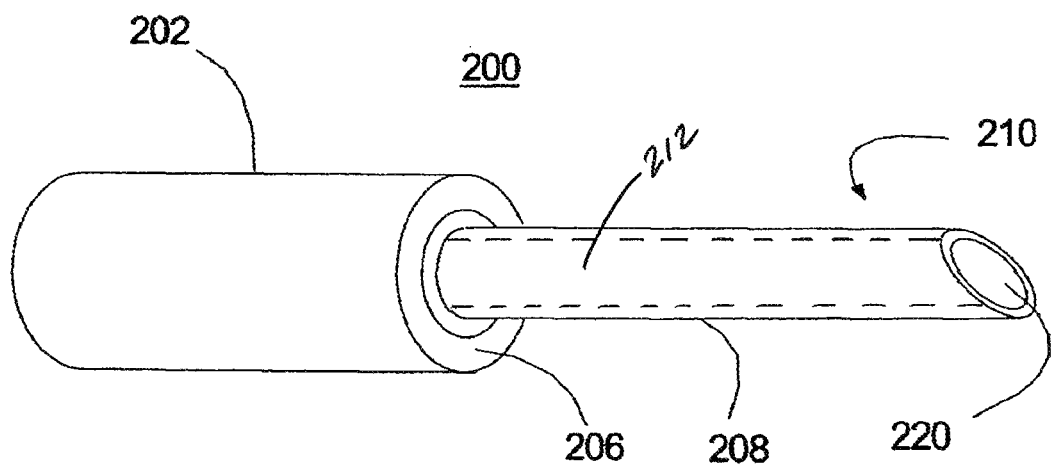
FIG. 2 illustrates an optical fiber having an output end being a fiber core with one cladding layer with a side fire surface thereon.

FIG. 2 depicts side fire optical fiber 200 with an output end 210 that may be used in the method of the present invention. Output end 210 has side fire surface 220 that is slanted at a given angle to the axis of optical fiber 202. A reflective coating may or may not be included on the surface 220. A predetermined length of optical fiber 200 has outer protective layer 206 removed to leave cladding layer 208 and core as shown. In the preferred embodiment, cladding layer 208 is composed of low OH, pure silica. Cladding material is originally deposited by a preferred method of plasma enhanced deposition on an outer surface of core material to make a preform(not shown) which is drawn to produce optical fiber 200. During the deposition process the percentage of fluorine is reduced so that the material is low OH, pure silica further from core 212 than at the core/cladding interface After drawing of the fiber, capillary tube 312 (FIG. 3) is fused to cladding layer 208 as will be disclosed hereinafter.

Figure 3:
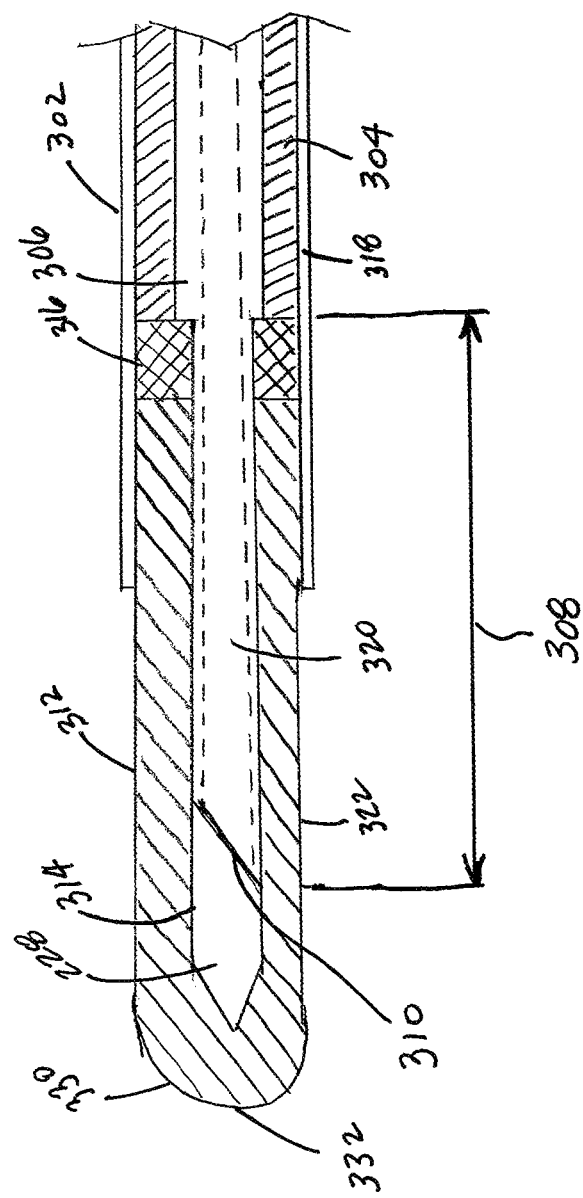
FIG. 3 illustrates by cross sectional view an optical fiber output tip of the present invention.

FIG. 3 illustrates optical fiber output tip 300 having a side fire feature. Optical fiber 302 being of conventional design has a protective or buffer layer 304 removed to leave cladding layer 306 on output end 308. On a distal end of output end 308, side fire surface 310 is formed and is of conventional design. The slant angle itself may range from 30 to 50 degrees as is conventional. Due to the diameter of the optical fiber, multi-mode reflections at side fire surface 310 provide an output beam that is somewhat projecting forward and is spreading out as it leaves output tip 300 at a range of angles, typically 70-100 degrees from the fiber axis. To further enhance the reflective power of surface 310 a reflective layer may be formed thereon, as is known in the optical arts.

Onto output end 308, capillary tube 312 having inside hole 314 being of close fit about output end 308 is fused to outer most surface region of clad layer 306. A void 228 is formed in the capillary tube between the side fire surface 310 and the capillary tube 312. A $CO_2$ laser may be used to fuse tube 312 to output end 308. This fusing process, is performed in such a way that bubbles or air gaps do not exist between the clad layer 306 and tube 312. Bonding section 316 secures tube 312 to protective layer 304 of optical fiber 302 to prevent undue strain on output end 308. Shrink tube 318 further protects the output tip 300 and is placed over section of tube 312, bonding section 316 and optical fiber 302.

Core 320 in the output section 308 is composed of silica having an index of refraction of $n_1$; clad layer 306 is also composed of silica and has an index of refraction of $n_2$ which at the interface with the core is less than $n_1$, but increases toward the outward edge of the cladding to a value equal to pure silica. Reference is made to FIG. 4 that shows a relationship between the indexes of refraction in the different sections of the output end 308. In this scheme, the core material 320 can be pure silica or a Germanium doped silica. The cladding material 306 would be a fluorine-doped silica. Further in the case of the doped core, the cladding material could be pure silica too. In the latter case the cladding would have a uniform refractive index across its thickness that would match the refractive index the tubing material 312 as the tube is also pure silica as noted throughout this specification.

To insure a minimum of reflection losses at the clad/tube interface, refractive indices are matched and care is taken to not permit formation of bubbles and air gaps at the interface between clad 306 and tube 312 during the fusion process. Capillary tube 312 is also composed of silica and has an index of refraction of $n_3$. The silica at the outer edge of clad layer 306 and in tube 312 is preferably pure silica, that is having the same refractive index, $n_3$. During the deposition of clad layer 306, when it is a fluorine-doped silica, the amount of fluorine is reduced so that at the fusing interface, clad layer is low OH, pure silica, and has essentially the same index of refraction as tube 312, also composed of low OH, pure silica.

To insure that the clad at the interface and the tube are essentially continuous mechanically and optically after fusing, the thermal behavior of the two facing surfaces shall be as equivalent as possible. Matching refractive indices is one measure to achieve this equivalence. Since glass is a viscous liquid its manufacturing process can also affect its thermodynamic properties, thus in a further embodiment, the manufacturing process of the tube can be made essentially the same as the outer surface layer of the cladding. That is, the thermal history of the outermost layer of the cladding is substantially equivalent to the thermal history of the inner surface of the tube.

In an additional preferred embodiment a more robust side firing distal end can be produced by further processing. The laser energy output area, being surface 322, is heat treated to create a more durable surface to high power laser energy and for mechanical properties. Surface 322 may be heat treated by a laser beam such as a $CO_2$ laser provides.

Sealed end section 330 is a distal section of capillary tube 312. The distal section is heated and closed to form sealed end section 330. Front tip 332 is rounded.

The present invention is further illustrated by the following examples, but is not limited thereby:

Example 1

In accord with the present invention, a medical laser with a maximum average power of 100 Watts and having an output wavelength of 2150 nm can be used in the treatment of BPH. Lasing can be performed using a 550 μm core with cladding layer 306 of 715 μm diameter, with a cladding to core ratio of 1.3. Optical fiber 302 has a diameter of 1950 μm, for example. Optical fiber output tip 300 can be positioned close to the target tissues such as a prostrate gland by a rigid endoscope, for example, with water as an irrigant to further cool the tip and help remove material as it is ablated, or degraded during high power operation.

Preferred embodiments may also be used to transmit high power laser energy from diode lasers operating at 980 nm or 1460 nm with power levels from 50 to about 250 Watts. Using fibers of similar size to that described above various medical treatments including treatment of BPH can be done very effectively, quickly and without requiring more than local anesthesia for the patient.

In a typical mode of operation, from FIG. 1, optical fiber 106 delivers laser energy from laser source 102 to a handpiece, endoscope, or similar instrument for positioning the fiber's distal output end 114 in close proximity, in direct contact with, or inside/within the target tissue. It is preferred that the handpiece, endoscope, or similar instrument have sufficient channels to accommodate the flow and removal of irrigant and/or debris from the treatment site, endoscopic instruments, aspirators, light guides, image guides, or other sensor and/or detection means. Benefits from using, for example, a 980 nm diode laser, instead of a Ho:YAG laser, are somewhat greater depth penetration, photocoagulation leading to a substantially blood free operating area.

Having described preferred embodiments of the invention with reference to the accompanying drawings, it is to be understood that the invention is not limited to the precise embodiments, and that various changes and modifications may be effected therein by one skilled in the art without departing from the scope or spirit of the invention according to the appended claims.

What is claimed is:

1. An optical fiber device having a side fire output tip for transmitting high power laser energy in urology treatments, consisting of:
    an optical fiber having a core a cladding over the core, and a protective layer over the cladding, wherein the core and the cladding define a core/cladding interface, the cladding diameter to core diameter ratio is within the range of 1.3 to 1.5, said optical fiber having an input end and an output end configured to transmit high power laser energy within the range of 50 to 300 Watts;
    said output end of said optical fiber being of a predetermined axial length and having an outer surface on the cladding and a side firing surface formed on the distal end of the output end, wherein said output end of said optical fiber is devoid of the protective layer on the outer surface of the cladding within the predetermined axial length;
    said cladding comprising fluorine doped silica, wherein the percentage of flourine is less, further from the core than adjacent to the core/cladding interface;
    wherein at the core/cladding interface, the refractive index of an inner surface of the cladding is lower than the refractive index of said core, and the refractive index of an outer surface of the cladding is higher than the refractive index of the inner surface of the cladding'
    a capillary tube attached to said output end of said optical fiber on the outer surface of said cladding, said capillary tube having a hole at a proximal end for the acceptance of said output end of said optical fiber, wherein the inner surface of the capillary tube is fused to the cladding along the predetermined length of the cladding and defining a cladding/capillary tube interface without bubbles or air gaps at the cladding/capillary tube interface, and having a sealed end section being formed from a distal end section of said capillary tube;
    a void located between said side fire surface and said sealed end section,
    wherein, at the cladding/capillary tube interface, the refractive index of an inner surface of said capillary tube is the same as the refractive index of said outer surface of said cladding;
    a shrink tube covering a proximal section of the capillary tube, the cladding/capillary tube interface and the protective layer; and at least one laser connectable to the input end of the optical fiber.

2. The optical fiber device according to claim 1 wherein said cladding outer surface and said capillary tube inner surface are composed of low OH, pure silica.

3. The optical fiber device according to claim 1 wherein the at least one laser connectable to the input end of the optical fiber is selected from a Holmium:YAG laser, a 980 nm diode laser, a 532 nm or KTP laser, and a 1460 nm diode laser.

4. The optical fiber device according to claim 1 wherein said output area is heat treated with a $CO_2$ laser.

5. The optical fiber device of claim 1 wherein the index of refraction of the cladding increases radially in the direction from the inner diameter to the outer diameter of the cladding.

6. The optical fiber device of claim 1 wherein the percentage of fluorine decreases radially in the direction from the inner diameter to the outer diameter of the cladding.

7. The optical fiber device of claim 1 wherein at the cladding/capillary tube interface, said inner surface of said capillary tube and said outer surface of said cladding are thermally matched, having equivalent fictive temperatures.

8. The optical fiber device of claim 1 wherein the capillary tube is thermally fused to the cladding along the predetermined length of the cladding.

9. An optical fiber device having a side fire output tip for transmitting high power laser energy in urology treatments, consisting of:
    an optical fiber having a core, a cladding including a clad layer surrounding the core, the core and the clad layer defining a core/clad layer interface, and a protective layer over the clad layer, wherein an output end of the optical fiber is devoid of the protective layer on an outer surface of the clad layer;

a capillary tube fused to the outer surface of the clad layer and defining a clad layer/capillary tube interface therebetween along a predetermined length of the clad layer without bubbles or air gaps at the clad layer/capillary tube interface, wherein the cladding diameter to core diameter ratio is at least 1.2, the optical fiber further comprising an input end and an output end configured to transmit high power laser energy within the range of 50-300 Watts, wherein the output end has a side firing surface formed thereon, and wherein the capillary tube has a sealed end section and a sealed space formed between the side firing surface and the sealed end section;

wherein the clad layer comprises fluorine doped silica and the percentage of fluorine is less further from the core than adjacent to the core/clad layer interface, the refractive index of the clad layer at the core/clad layer interface is lower than the refractive index of the core, the refractive index of the clad layer at the outer surface thereof is higher than at the core/clad layer interface, and at the clad layer/capillary tube interface, the refractive index of the outer surface of the clad layer is the same as the refractive index of an inner surface of the capillary tube; and wherein at the clad layer/capillary tube interface, the inner surface of the capillary tube and the outer surface of the cladding are thermally matched, thermal behavior of the inner surface of the capillary tube and the outer surface of the cladding being substantially equivalent;

a shrink tube covering a proximal section of the capillary tube, the clad layer/capillary tube interface and the protective layer; and at least one laser connectable to the input end of the optical fiber.

10. The optical fiber of claim 9, wherein cladding diameter to core diameter ratio is within the range of 1.3 to 1.5.

11. The optical fiber device of claim 9, wherein the at least one laser connectable to the input end of the optical fiber is selected from a Holmium:YAG laser, a 980 nm diode laser, a 532 nm or KTP laser, and a 1460 nm diode laser.

* * * * *